United States Patent
Williams

[11] Patent Number: 5,935,083
[45] Date of Patent: *Aug. 10, 1999

[54] DEVICE FOR BODY FLUID PRESSURE MEASUREMENT

[76] Inventor: Paul A. Williams, 2707 Southampton Rd., Carlsbad, Calif. 92008

[ * ] Notice: This patent issued on a continued prosecution application filed under 37 CFR 1.53(d), and is subject to the twenty year patent term provisions of 35 U.S.C. 154(a)(2).

[21] Appl. No.: 08/675,452

[22] Filed: Jul. 3, 1996

[51] Int. Cl.[6] .................................................. A61B 5/00
[52] U.S. Cl. ..................... 600/561; 600/488; 604/158; 604/51
[58] Field of Search ................... 600/561, 485, 600/486, 488, 498, 583, 584, 566, 466; 604/158, 51, 53

[56] References Cited

U.S. PATENT DOCUMENTS

| | | | |
|---|---|---|---|
| 3,610,228 | 10/1971 | Temkin | 128/748 |
| 3,670,729 | 6/1972 | Bennett et al. | |
| 3,920,002 | 11/1975 | Dye et al. | 128/748 |
| 3,942,382 | 3/1976 | Hok | 600/488 |
| 4,846,191 | 7/1989 | Brockway et al. | 128/748 |
| 4,924,872 | 5/1990 | Frank | 128/673 |
| 4,947,856 | 8/1990 | Beard | 128/673 |
| 5,105,820 | 4/1992 | Moriuchi et al. | 128/673 |
| 5,203,866 | 4/1993 | Islam | 606/186 |
| 5,205,828 | 4/1993 | Kedem | 604/158 |
| 5,218,965 | 6/1993 | Ring | 128/673 |
| 5,573,807 | 11/1996 | Bobo, Sr. | 128/748 |

*Primary Examiner*—Robert A. Clarke
*Assistant Examiner*—V. Srivastava
*Attorney, Agent, or Firm*—Lyon & Lyon LLP

[57] ABSTRACT

A device for measuring body fluid pressure, such as blood pressure, muscle compartment pressure, and spinal column pressure, is herein described. An invasive implement is inserted into a body area, and a fluid path extends from the body area into a fluid channel in the device. A valve is used to control the flow of fluid through the device and a pressure sensor is placed adjacent to the fluid channel, with the pressure sensor and/or a sealant gel forming a portion of the fluid channel. With the valve closed, pressure builds in the fluid channel and the pressure sensor detects the resulting pressure, and a pressure transducer and supporting electronics converts and communicates the pressure measurement. With this device the pressure sensor can detect pressure without contacting the fluid, so therefore a pressure can be taken with a minimum of fluid extraction. If fluid extraction is desired, the valve is opened and fluid flows from the body area to a fluid port where the fluid may be collected.

15 Claims, 2 Drawing Sheets

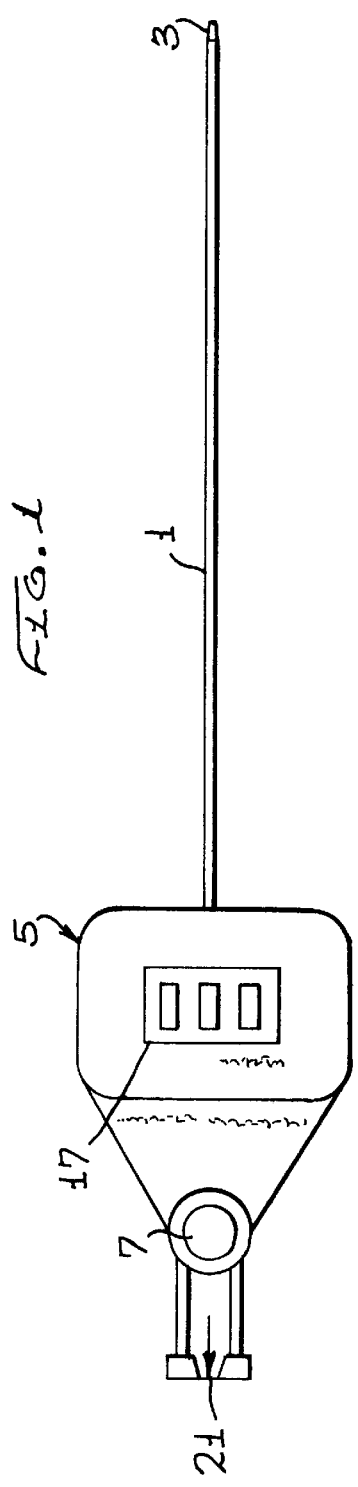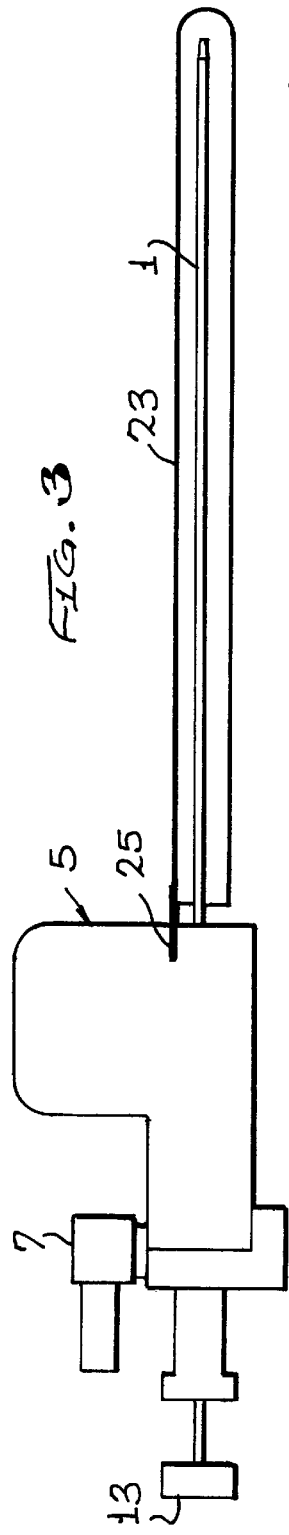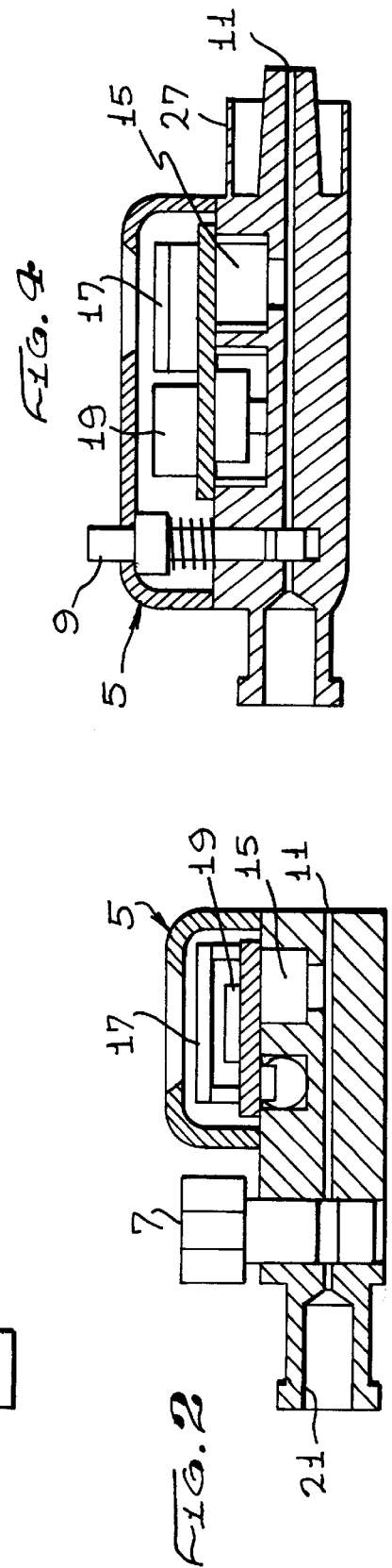

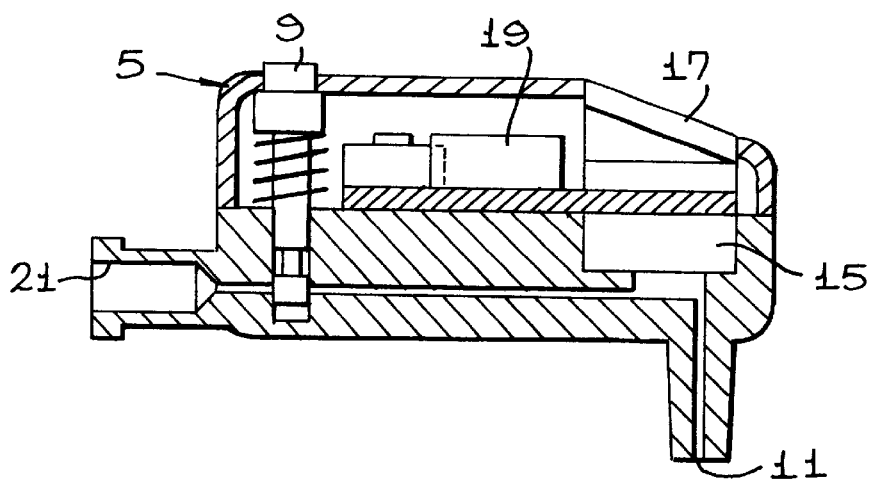
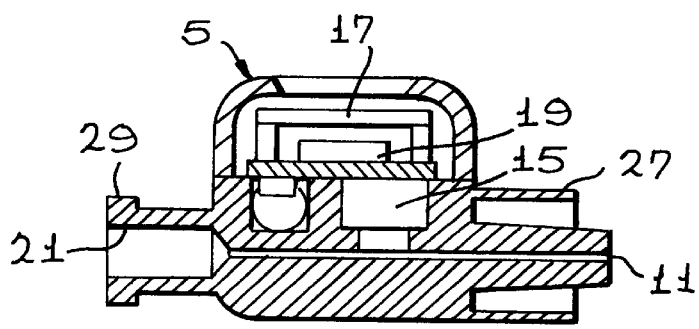
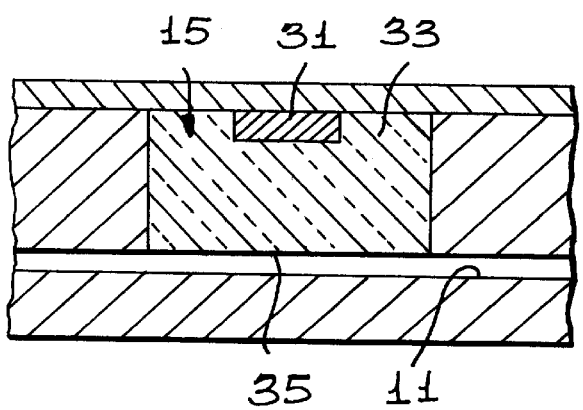
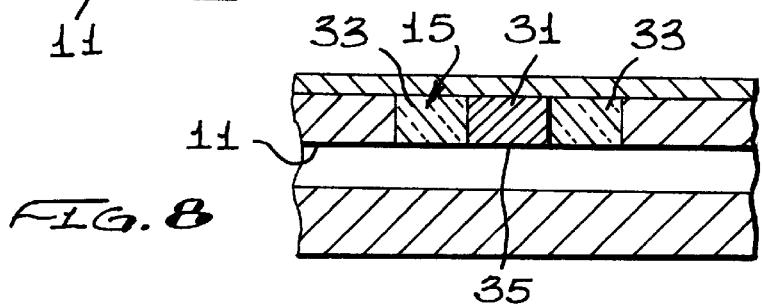

DEVICE FOR BODY FLUID PRESSURE MEASUREMENT

FIELD OF THE INVENTION

The field of invention relates to invasive pressure measuring devices for body fluid pressures.

BACKGROUND OF THE INVENTION

Medical practitioners often need to invasively measure fluid pressure within a body. Commonly, blood pressure, muscle compartment pressure, and spinal column pressure are taken to assist in the diagnosis or treatment of patients. For those with spinal problems, a medical practitioner often performs a procedure, commonly called a spinal tap, to invasively enter the spinal column, withdraw some spinal fluid, and measure the pressure within the spinal column. The spinal tap is more formally called the Lumbar Puncture Procedure (LPP).

The technology for the Lumbar Puncture Procedure has changed little since it was first performed by Quincke in 1891. This procedure removes Cerebrospinal Fluid (CSF) from within the spinal column for bacteriologic evaluation and measures the CSF pressure to diagnose the patient's general neurologic condition. Unusually high or low CSF pressures indicate some loss of the patients auto-regulation (self-regulating capacity) and general loss of neurologic function.

The current invasive implement used in LPP is a small needle cannula. An obturator or stilette is positioned inside the needle to prevent matter from blocking the internal channel of the needle as it penetrates tissue. The needle is inserted between the lumbar vertebrae just below the termination of the spinal cord, piercing the dura and reaching the fluid filled sub-dural space in the spinal column. Once located in this space, the obturator or stilette is removed, allowing CSF to flow from the needle tip and out the proximate end of the needle. The proper location of the needle is ascertained by this outflow of CSF.

A stopcock and open tube manometer now may be connected to the proximal end of the needle cannula. With the stopcock in the open position, the manometer fills with CSF until its elevation (Pressure Head) equals the pressure inside the spinal column. Equalizing the pressure can take between 5 and 15 minutes. This height is converted to a pressure unit (e.g. mmHg or cmH$_2$O) and is defined as the patient's "Opening Pressure". After this pressure measurement, some of the fluid contents of the manometer can then be removed through a release valve into a collection vial for bacteriologic evaluation, such as diagnosis for spinal meningitis.

Once a sufficient quantity of CSF has been removed for analysis (typically 9 to 15 ml) the manometer can be re-filled as above (an additional 5 to 15 minutes). Once stabilized this new pressure measurement on the manometer is said to be the patients "Closing Pressure". If the difference between the Opening and Closing pressures is large, this may indicate a spinal blockage that prevents the normal auto-regulation function that should compensate for the loss of fluid and maintain a constant CSF pressure. Many physicians skip this "Closing Pressure" portion of the procedure to save time even though it is important in assessing the patients condition.

If a blockage is diagnosed by a large drop in CSF pressure, then the removal of an excessive amount of CSF may cause patient harm: if too much fluid is removed the pressure gradients between the brain and spinal column may cause traction and damage to the brain stem. In a blockage case, it would be preferable that the pressure measurement be made in a manner minimizing the removal of CSF. In fact, if the patient's CSF pressure is believed to be too high this procedure is contraindicated.

Also, using the LPP method takes considerable time and effort. The longer the needle cannula is left in the patient, the more likely an infection will result. Additionally, the extended procedure time contributes to a common post operative complication called "Post Lumbar Puncture Headache". One of the primary causes of the complication is the continued leakage of CSF from the puncture site. This causes continued traction on the spinal cord and brain stem, resulting in patient headaches. As a result, the patient must remain hospitalized in a prone position for days, adding to the cost and discomfort of these patients.

The current manometer systems are typically over 18 inches tall. As a result practitioners have a difficult time holding the manometer/needle system in a stable position for the 10–20 minute duration of the procedure. This "Level Arm" effect contributes to additional tearing of the tissues that increase the amount of CSF leakage.

There have been attempts to use alternative detection systems rather than manometer systems in the measuring of body fluid pressures, such as Tempkin et al., U.S. Pat. No. 3,610,228, Moriuchi et al., U.S. Pat. No. 4,790,193, and Davis et al., U.S. Pat. No. 4,817,629. Each of these referenced devices requires either a complex valve switching system, a chamber that must be filled with a fluid, or an external device for priming, with corresponding limitations on usefulness.

SUMMARY OF THE INVENTION

The present invention provides a device for measuring body fluid pressure in a body area using an invasive technique.

In a first, separate aspect of the invention, a housing has a fluid channel with an opening. The opening allows the body fluid to communicate with the fluid channel, and a valve is on the fluid channel. A pressure sensor is placed adjacent to the fluid channel whereby the pressure sensor extends to the fluid channel and forms a portion of the fluid channel wall.

In a second, separate aspect of the invention, the device of the first aspect is contemplated where the fluid channel extends through the housing with the cross-section of the fluid channel remaining substantially constant.

In a third, separate aspect of the invention, the device of the first aspect is contemplated with a substantially rigid obturator or stilette positionable through the fluid channel.

BRIEF DESCRIPTIONS OF THE DRAWINGS

FIG. 1 shows a top view of a single-use preferred embodiment where the needle cannula is permanently attached to a housing.

FIG. 2 is a cross sectional view of the housing in FIG. 1.

FIG. 3 is a side view of the device in FIG. 1, with a removable sheath covering the needle cannula. The removable sheath is shown as a cross-section.

FIG. 4 shows a cross sectional view of an alternate preferred embodiment that uses a push-button valve and a removable needle canula.

FIG. 5 shows a cross sectional view of an alternate preferred embodiment that uses a push-button valve, a removable needle canula, and has a bend in the fluid channel.

FIG. 6 shows a cross sectional view of an alternate preferred embodiment that uses a removable needle canula and a removable valve.

FIG. 7 shows a close-up view of the pressure transducer embedded in a pressure translating gel, with the pressure translating gel forming a portion of the fluid channel wall.

FIG. 8 shows a close-up view of the transducer embedded in a gel, with the pressure transducer forming a portion of the fluid channel wall.

DESCRIPTION OF THE PREFERRED EMBODIMENT

A preferred embodiment of the present invention is shown in FIGS. 1, 2 and 3. This device has a needle cannula 1 permanently attached to a housing 5. The needle cannula 1 has a tip end 3 shaped to penetrate tissue with an opening that extends into an internal fluid channel. The needle's fluid channel extends from the tip end 3 through to the housing 5, and connects with the housing fluid channel 11. A pressure sensor 15 is placed adjacent to the fluid channel 11, which communicates to supporting electronics 19. The pressure sensor 15 in the preferred embodiment has a pressure transducer that contains a strain gage, but those skilled in the art will recognize several alternatives for fluid pressure measurement. The supporting electronics 19 are well known and comprise a power source, electronics to convert the signal from the pressure sensor 15 into pressure data, and the electronics to drive an output device. In the preferred embodiment, the output device is an LCD digital display, but those skilled in the art will recognize several alternatives to a digital display, such as meters, LCD bars, audio alarms, communication to an external device, and other alternatives.

The housing fluid channel 11 extends through the housing 5 and connects to the fluid port 21. The housing also has a stopcock valve 7 in the housing fluid channel 11, placed so the pressure sensor 15 is placed between the tip end 3 and the stopcock valve 7. When the valve is open, any fluid entering the tip end 3 will pass unobstructed through the needle fluid channel, the housing fluid channel 11, and out the fluid port 21. When closed, fluid entering the tip end 3 will not pass through the housing 5, but will be restricted such that a pressure will build in the housing fluid channel which will be detected by the pressure sensor 15.

Detail of the pressure sensor 15 is shown in FIGS. 7 and 8. Here, a pressure transducer 31 contains a strain gage for measuring pressure. The transducer 31 may be embedded in a gel 33 that seals the opening 35 in the fluid channel 11. Those skilled in the art will recognize several materials and alternatives suitable for such a purpose. In FIG. 8, the gel 33 is positioned about the transducer 31 such that the pressure transducer 31 extends to the fluid channel 11 and forms a portion of the fluid channel 11. The transducer may be coated or layered with a sealant material that contacts the matter in the fluid channel 11 and translates the pressure to the pressure transducer 31. Alternatively, as shown in FIG. 7, the gel 33 may seal and fill the opening 35, with the gel forming part of the fluid channel wall. In this alternative, the gel acts to translate the pressure in the fluid channel 11 to the transducer 31.

The housing fluid channel 11 in the preferred embodiment needs no priming, that is, no external fluid is needed to prepare the device to take a pressure reading. In fact, the pressure sensor 15 will detect pressure and permit the pressure transducer 31 to take a measurement without any direct contact with a fluid. If a body fluid under pressure is placed at the tip end 3 with the valve 7 closed, the fluid will not flow through the device, but will build an air pressure proximate to the pressure sensor 15. A pressure measurement can then be taken without any fluid having flown through the device. Additionally, the cross-sectional area of the housing fluid channel 11 in the preferred embodiment remains substantially constant, as it does not need a chamber or other void to effectuate the sensing of pressure. Not needing a chamber or void reduces the amount of fluid extracted during a procedure using the device.

To use this device, a protective needle sheath 23 may need to be removed from the needle cannula 3. A sheath tab 25 may be attached to the protective sheath 23, which will be pulled from the housing 5 when the protective sheath 23 is removed. This tab may be coupled to the supporting electronics 19 in a manner that initiates the application of power to the device. This automatic power-on process is especially useful when using single-use devices in time-critical situations.

Although the preferred embodiment may be used to measure several body fluid pressures, such as blood pressure, muscle compartment pressure, and spinal column pressure, the preferred embodiment will be described in the context of taking spinal column pressure. Once the protective sheath 23 is removed and the device activated, the practitioner inserts the needle cannula into the spinal area of the patient. Since the needle cannula 3 will be penetrating several layers of tissue, is possible that tissue may enter and block the tip end 3 or the needle fluid channel. This blockage is avoided by the use of a stilette or obturator. As shown in FIG. 3, the valve is placed in the open position, creating a straight unobstructed channel from the fluid port 21 to the tip end 3. A stilette or obturator is inserted through the fluid port, into the housing fluid channel, and extending to the tip end 3. Therefore, as the needle cannula is inserted, tissue is kept out of the needle fluid channel.

Once the needle cannula is properly placed in the spinal column, the obturator or stilette is removed, and fluid flows from the tip end 3 to the fluid port 21. The presence of this fluid flow alerts the practitioner that the needle cannula 3 is properly placed, and then the stopcock valve 7 is closed. Alternately, the valve 7 can be closed immediately, and a pressure reading taken before the fluid begins flowing through the device. With the valve closed, the housing fluid channel quickly reaches the same pressure as present at the tip end 3. This opening pressure is detected by the pressure sensor 15, converted to meaningful information by the pressure transducer 31 and the supporting electronics 19, and displayed to the practitioner via the digital display 17. If the pressure is too high, the practitioner may decide that the procedure needs to end now, as release of CSF may severely injure the patient. If the pressure indicates that it is safe to extract CSF, the stopcock valve is opened and fluid collected from the fluid port 21. Once the fluid is collected, the stopcock valve is once again closed and the closing pressure read. The device is now removed from the patient. Since this preferred embodiment is for a single-use device, it is discarded. Those skilled in the art will recognized that this device could alternatively be made reusable.

FIG. 4 shows the housing 5 of an alternate preferred embodiment. In this embodiment the needle cannula is removable, allowing for the selection of a needle cannula independent from the housing 5. Additionally, having the needle cannula removable facilitates making the housing 5 reusable while still using disposable needle cannulas. The needle cannula is attached to the housing 5 with a needle attachment mechanism 27. Needle attachment mechanisms are well known in the art, with a lure lock as a common example. This embodiment also uses a push button valve 9 that is normally closed, and is pressed to open for insertion of an obturator or for the release of fluid. FIG. 6 shows another preferred embodiment similar to the one shown in FIG. 4, except a valve is removably attached to the housing 5 via a locking mechanism 29 at the fluid port 21.

FIG. 5 shows the housing 5 of another alternate preferred embodiment. Here, the housing fluid channel 11 is not straight and unobstructed. To use this device, a needle cannula, with an obturator, will be independently inserted into a patient. After the needle cannula is in place, the practitioner will remove the obturator, verify CSF flow, and connect the housing 5 to the in-place needle cannula.

Although the preferred embodiments discussed above relate to sampling and measuring spinal fluid pressure, the invention is not so limited. While embodiments and applications of this invention have been shown and described, it would be apparent to those skilled in the art that many more modifications are possible without departing form the inventive concepts herein. The invention, therefore, is not to be restricted except in the spirit of the appended claims.

What is claimed is:

1. A device for measuring spinal fluid pressure using a needle cannula, comprising:

a housing including a fluid channel wall that defines a fluid channel, the housing including a tip end configured to receive the needle canula to allow spinal fluid to enter the housing and a fluid port configured to allow spinal fluid to exit the housing;

a valve located in said fluid channel between said tip end and said fluid port, the fluid channel wall having a constant cross-section from the valve to the tip end; and a pressure transducer at least partially forming said fluid channel wall between the tip end and the valve and adapted to take a static pressure measurement of the spinal fluid pressure with the valve closed using a minimal amount of spinal fluid.

2. The device of claim 1, wherein the valve is movable from an open position so that spinal fluid can exit the fluid port to a closed position so that pressure can build up in the fluid channel.

3. The device of claim 1, further including a hollow needle cannula attached to the tip end and coaxially aligned with the pressure transducer.

4. The device of claim 3, further including a sheath for the needle cannula and supporting electronics for the pressure transducer, a sheath tab coupling the sheath to the supporting electronics so that upon removing said tab power is initiated to said supporting electronics.

5. The device of claim 3, further including a substantially rigid obturator positionable in the hollow cannula and fluid channel.

6. A device for measuring spinal fluid pressure, comprising:

a housing including a fluid channel wall that defines a fluid channel, the housing including a tip end configured to allow spinal fluid to enter the housing and a fluid port configured to allow spinal fluid to exit the housing, a hollow needle cannula connected to the tip end of the housing and coaxially aligned with the fluid channel;

a valve located in said fluid channel between said tip and said fluid port, the fluid channel wall having a constant cross-section from the valve to the tip end; and a pressure transducer located in said fluid channel between said tip end and fluid port and coaxially aligned with the hollow needle cannula so that a pressure measurement of the spinal fluid pressure can be made using a minimal amount of spinal fluid.

7. The device of claim 6, wherein the valve is movable from an open position so that spinal fluid can exit the fluid port to a closed position so that pressure can build up in the fluid channel.

8. The device of claim 6, further including a substantially rigid obturator positionable in the hollow cannula and fluid channel.

9. The device of claim 6, further including a sheath for the needle cannula and supporting electronics for the pressure transducer, a sheath tab coupling the sheath to the supporting electronics so that upon removing said tab power is initiated to said supporting electronics.

10. A method of measuring spinal fluid pressure, comprising:

providing a device for measuring spinal fluid pressure including a housing having a fluid channel wall that defines a fluid channel, the housing including a tip end configured to allow spinal fluid to enter the housing and a fluid port configured to allow spinal fluid to exit the housing, a hollow needle cannula attached to the tip end, a substantially rigid obturator positionable in the hollow cannula and fluid channel, a valve located in said fluid channel between said tip end and said fluid port, the fluid channel wall having a constant cross-section from the valve to the tip end, a pressure transducer at least partially forming said fluid channel wall between the tip end and the valve;

inserting the needle cannula into a spinal area of the patient with the obturator positioned in the hollow cannula;

removing the obturator from the needle cannula; and taking a static pressure measurement of the spinal fluid pressure with the valve closed using a minimal amount of spinal fluid.

11. The method of claim 10, wherein the step of taking a static pressure measurement includes taking a static pressure measurement based on the static air pressure built up in the housing fluid channel around the pressure transducer without any liquid passing through the housing fluid channel.

12. The method of claim 10, further including moving the valve to the open position in order to collect spinal fluid from the fluid port.

13. The method of claim 12, further including closing the valve and tag another pressure reading.

14. The method of claim 10, wherein the needle cannula is coaxially aligned with the pressure transducer.

15. The method of claim 10, further including a sheath for the needle cannula, supporting electronics for the pressure transducers, and a sheath tab coupling the sheath to the supporting electronics, the method further including initiating power to said supporting electronics by removing said sheath.

* * * * *